US010029969B2

(12) United States Patent
Ohkuma et al.

(10) Patent No.: US 10,029,969 B2
(45) Date of Patent: Jul. 24, 2018

(54) METHOD OF PRODUCING OPTICALLY-ACTIVE ALDEHYDE

(71) Applicant: TAKASAGO INTERNATIONAL CORPORATION, Tokyo (JP)

(72) Inventors: Takeshi Ohkuma, Hokkaido (JP); Noriyoshi Arai, Hokkaido (JP); Kazuhiko Matsumura, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/767,744

(22) PCT Filed: Mar. 6, 2014

(86) PCT No.: PCT/JP2014/055755
§ 371 (c)(1),
(2) Date: Aug. 13, 2015

(87) PCT Pub. No.: WO2014/136868
PCT Pub. Date: Sep. 12, 2014

(65) Prior Publication Data
US 2015/0376102 A1  Dec. 31, 2015

(30) Foreign Application Priority Data
Mar. 6, 2013 (JP) ................. 2013-044065

(51) Int. Cl.
*C07C 45/51* (2006.01)
*C07B 53/00* (2006.01)
(52) U.S. Cl.
CPC ............ *C07C 45/512* (2013.01); *C07B 53/00* (2013.01); *C07C 45/51* (2013.01); *C07B 2200/07* (2013.01); *C07C 2601/14* (2017.05)
(58) Field of Classification Search
None
See application file for complete search history.

(56) References Cited

U.S. PATENT DOCUMENTS

| | | | |
|---|---|---|---|
| 6,031,145 A | 2/2000 | Commereuc et al. | |
| 2004/0092388 A1* | 5/2004 | Shimizu | B01J 31/2428 502/150 |
| 2007/0073065 A1* | 3/2007 | Fujiwara | C07F 9/65517 549/206 |
| 2011/0295031 A1 | 12/2011 | Itoh et al. | |

FOREIGN PATENT DOCUMENTS

| | | |
|---|---|---|
| JP | 56-083434 A | 7/1981 |
| JP | 11-19518 A | 1/1999 |
| JP | 2009-269868 A | 11/2009 |
| JP | 2011-246366 A | 12/2011 |

OTHER PUBLICATIONS

Robert C. van der Drift, et al., "Homogeneously catalysed isomerisation of allylic alcohols to carbonyl compounds", Journal of Organometallic Chemistry 650 (2002), pp. 1-24.
Ramalinga Uma, et al., "Transposition of Allylic Alcohols into Carbonyl Compounds Mediated by Transition Metal Complexes", Chem. Rev. 2003, 103, pp. 27-51.
Gregory C. Fu, "Recent Advances in Rhodium(I)-Catalyzed Asymmetric Olefin Isomerization and Hydroacylation Reactions", Modern Rhodium-Catalyzed Organic Reactions (Ed.: P.A. Evans), Wiley-VCH, Weinheim, 2005, pp. 79-91.
Ken Tanaka, et al., "Enantioselective Isomerization of Allylic Alcohols Catalyzed by a Rhodium/Phosphaferrocene Complex", J. Am. Chem. Soc., vol. 122, No. 40, 2000, American Chemical Society, pp. 9870-9871.
Ken Tanaka, et al., "A Versatile New Catalyst for the Enantioselective Isomerization of Allylic Alcohols to Aldehydes: Scope and Mechanistic Studies", J. Org. Chem. 2001, 66, American Chemical Society, vol. 66, No. 24, pp. 8177-8186.
Carlo Botteghi, et al., "Asymmetric Isomerization of Allyl Alcohols with Rhodium(I)-Chiral Phosphine Complexed", Gazzetta Chimica Italiana, 106, 1976, pp. 1131-1134.
Kazuhide Tani, "Asymmetric isomerization of allylic compounds and the mechanism", Pure & Appl. Chem., vol. 57, No. 12, 1985, pp. 1845-1854.
Luca Mantilli, et al., "Platinum Metals in the Catalytic Asymmetric Isomerization of Allylic Alcohols", Chem. Lett. 40, 2011, The Chemical Society of Japan, pp. 341-344.
Christian Chapuis, et al., Synthesis of Citronellal by RhI-Catalysed Asymmetric Isomerization of N,N-Diethyl-Substituted Geranyl- and Nerylamines or Geraniol and Nerol in the Presence of Chiral Diphosphino Ligands, under Homogeneous and Supported Conditions), Helvetica Chimica Acta, vol. 84, 2001, pp. 230-242.
Fabien Boeda, et al., "First rhodium/phosphoramidite complex-catalyzed enantioselective isomerization of allylic alcohols into aldehydes", Tetrahedron Letters, 2006, 47, pp. 5021-5024.
Luca Mantilli, et al., "Iridium-Catalyzed Asymmetric Isomerization of Primary Allylic Alcohols", Angew. Chem. Int. Ed. 2009, 48, Wiley-VCH Verlag GmbH & Co. KGaA, Weinheim, pp. 5143-5147.
Luca Mantilli, et al., "Expanded scope for the iridium-catalyzed asymmetric isomerization of primary allylic alcohols using readily accessible second-generation catalysts", Chem. Commun., 2010, 46, The Royal Society of Chemistry, pp. 445-447.
Luca Mantilli, et al., "Improved Catalysts for the Iridium-Catalyzed Asymmetric Isomerization of Primary Allylic Alcohols Based on Charton Analysis", Chem. Eur. J. 2010, 16, Wiley-VCH Verlag GmbH&Co. KGaA, Weinheim, pp. 12736-12745.
Adrien Quintard, et al., "Access to High Levels of Molecular Complexity by One-Pot Iridium/Enamine Asymmetric Catalysis", Angew. Chem. Int. Ed. 2011, 50, Wiley-VCH Verlag GmbH & Co. KGaA, Weinheim , pp. 2354-2358.

(Continued)

*Primary Examiner* — Rosalynd Ann Keys
(74) *Attorney, Agent, or Firm* — Sughrue Mion, PLLC

(57) ABSTRACT

A method for producing, in a few simple steps, a specific optically active aldehyde represented by the general formula (1), in which * is an asymmetric carbon atom, includes asymmetrically isomerizing a specific allyl alcohol represented by the general formula (2) in the presence of a ruthenium complex and a base.

3 Claims, No Drawings

(56) References Cited

OTHER PUBLICATIONS

Sara Bovo, et al., "A New Enantioselective Catalytic Route to Florhydral", Synthesis, 2008, No. 16, Georg Thieme Verlag Stuttgart, pp. 2547-2550.
Jia-Qi Li, et al., "Highly Enantioselective Asymmetric Isomerization of Primary Allylic Alcohols with an Iridium-N,P Complex", Chem. Eur. J. 2011, 17, Wiley-VCH Verlag GmbH&Co. KGaA, Weinheim, pp. 11143-11145.
Angelino Doppiu, et al., "A New Route to Cationic Half-Sandwich Ruthenium(II) Complexes with chiral Cyclopentadienylphosphane Ligands", European Journal of Inorganic Chemistry, 2004, vol. 2004, pp. 2244-2252.
Georg Süss-Fink, et al., "Chiral modification of trinuclear ruthenium clusters with proline and cysteine derivatives. Synthesis, crystal structure, and catalytic properties of [($\mu_2$-H)Ru$_3$(CO)$_{10-}$ $_{(\mu2}$,$\eta^2$-OCNCH$_2$ CH$_2$CH$_2$CHCH$_2$OCH$_3$)] and [($\mu_2$-H)Ru$_3$(CO)$_9$($\mu_3$,$\eta^2$-N=CCH$_2$CH$_2$CHCH$_2$OCH$_3$)]", Journal of Organometallic Chemistry, 1989, vol. 379, Issue 3, 311-323.
Rouqiu Wu, et al., "Ruthenium-Catalyzed Asymmetric Transfer Hydrogenation of Allylic Alcohols by an Enantioselective Isomerization/Transfer Hydrogenation Mechanism", Angewandte Chemie International Edition, 2012, vol. 51, Issue 9, pp. 2106-2110.
Alba E. Diaz-Alvarez, et al., "Ruthenium-catalyzed reduction of allylic alcohols using glycerol as solvent and hydrogen donor", Catalysis Communications, 2011, vol. 13, Issue 1, pp. 91-96.
Istvan E. Marko, et al., "Novel and efficient Isomerization of Allylic Alcohols Promoted by a Tetrapropylammonium Perruthenate Catalyst", Angewandte Chemie International Edition, 1999 vol. 38, Issue 13-14, pp. 1960-1962.
International Search Report for PCT/JP2 014/055755 dated May 13, 2014 [PCT/ISA/210].
Written Opinion for PCT/JP2 014/055755 dated May 13, 2014 [PCT/ISA/237].
Communication dated Sep. 8, 2016, issued by the European Patent Office in counterpart European Patent Application No. 14760897.0.
Communication issued by the Japanese Patent Office on Jul. 18, 2017 in counterpart Japanese Patent Application No. 2015-504378.
Communication dated May 23, 2017 issued by the Japanese Patent Office in counterpart Japanese Patent Application No. 2014-547033.

* cited by examiner

METHOD OF PRODUCING OPTICALLY-ACTIVE ALDEHYDE

TECHNICAL FIELD

The present invention relates to a method for producing an optically active aldehyde. In more detail, the present invention relates to a novel production method that can produce an optically active aldehyde useful as medicines, agricultural chemicals, functional materials, fragrance or cosmetics, various chemicals, or starting materials or synthetic intermediates thereof, in high optical purity, in high yield and efficiently.

BACKGROUND ART

Heretofore, as a method of asymmetrically isomerizing an allyl alcohol to give an optically active aldehyde, there are known methods of using a transition metal complex as described in Non-Patent Documents 1 to 4. However, in these methods, the catalyst activity is low, and the optical purity of the resultant optically active aldehyde is not sufficiently satisfactory.

Further, there are known methods of using a complex of transition metal such as rhodium or ruthenium, as described in Non-Patent Documents 5 to 16. However, these methods require high substance specificity and therefore could not be said to be versatile methods.

Thus, heretofore, the realization of new synthetic method with high versatility for producing an optically active aldehyde, which enables highly-selective and high-yield production has been desired.

CITATION LIST

Non-Patent Literature

Non-Patent Document 1: J. Organomet. Chem., 2002, 650, 1-24
Non-Patent Document 2: Chem. Rev., 2003, 103, 27-51
Non-Patent Document 3: Modern Rhodium-Catalyzed Organic Reactions (Ed.: P. A. Evans). Wiley-VCH, Weinheim, 2005, pp. 79-91,
Non-Patent Document 4: Chem. Lett., 2011, 40, 341-344
Non-Patent Document 5: J. Am. Chem. Soc., 2000, 122, 9870-9871
Non-Patent Document 6: J. Org. Chem., 2001, 66, 8177-8186
Non-Patent Document 7: Gazz. Chim. Ital., 1976, 106, 1131-1134
Non-Patent Document 8: Pure Appl. Chem., 1985, 57, 1845-1854
Non-Patent Document 9: Helv. Chim. Acta, 2001, 84, 230-242
Non-Patent Document 10: Tetrahedron Lett., 2006, 47, 5021-5024
Non-Patent Document 11: Angew. Chem. Int. Ed., 2009, 48, 5143-5147
Non-Patent Document 12: Chem. Commun., 2010, 46, 445-447
Non-Patent Document 13: Chem. Eur. J., 2010, 16, 12736-12745
Non-Patent Document 14: Angew. Chem. Int. Ed., 2011, 50, 2354-2358
Non-Patent Document 15: Synthesis, 2008, 2547-2550
Non-Patent Document 16: Chem. Eur. J., 2011, 17, 11143-11145

SUMMARY OF THE INVENTION

Problems that the Invention is to Solve

An object of the present invention is to provide a method for producing an optically active aldehyde, in which an allyl alcohol is asymmetrically isomerized in the presence of a ruthenium complex and a base, as a means for solving the above-mentioned problems.

That is, the present invention makes it possible to produce an optically active aldehyde simply, in the small number of steps, in high optical purity, at a lower cost and in high yield.

Means for Solving the Problems

That is, the present invention relates to the following [1] to [3].

[1] A method for producing an optically active aldehyde represented by the formula (1):

[Chem. 1]

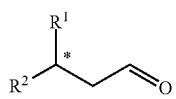

(1)

wherein $R^1$ and $R^2$ are each independently selected from the group consisting of an alkyl group having from 1 to 20 carbon atoms, which may have a substituent, an alkenyl group having from 2 to 20 carbon atoms, which may have a substituent, a 3- to 8-membered alicyclic group which may have a substituent, an aryl group having from 6 to 15 carbon atoms, which may have a substituent, and an aralkyl group having from 7 to 12 carbon atoms, which may have a substituent; $R^1$ and $R^2$ are groups different from each other, and * is an asymmetric carbon atom, the method comprising asymmetrically isomerizing an allyl alcohol represented by the formula (2) in the presence of a ruthenium complex and a base:

[Chem. 2]

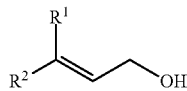

(2)

wherein $R^1$ and $R^2$ have the same meanings as described above.

[2] The production method according to the above [1], wherein the asymmetric isomerization is carried out using a ruthenium complex represented by the following general formula (3):

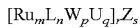

$[Ru_mL_nW_pU_q]Z_s$ (3)

wherein L is an optically active phosphine ligand; W is a hydrogen atom, a halogen atom, an acyloxy group, an aryl group, a diene or an anion; U is a hydrogen atom, a halogen atom, an acyloxy group, an aryl group, a diene, an anion or a ligand other than L; Z is an anion, an amine or an optically active nitrogen-containing compound; m, n and r are each independently an integer of from 1 to 5; p, q and s are each independently an integer of from 0 to 5; and p+q+s is 1 or more.

[3] The production method according to the above [1] or [2], wherein the base is a salt of an alkali metal or alkaline earth metal, or a quaternary ammonium salt.

Advantageous Effects of the Invention

The present invention is directed to a method for producing an optically active aldehyde useful as medicines, agricultural chemicals, functional materials, fragrance or cosmetics, various chemicals, or starting materials or synthetic intermediates thereof, simply, in the small number of steps, in high optical purity, at a lower cost and in high yield, and is industrially useful.

MODE FOR CARRYING OUT THE INVENTION

The present invention is described in detail hereinunder.

The method for producing an optically active aldehyde in the present invention is carried out according to the reaction shown below.

[Chem. 3]

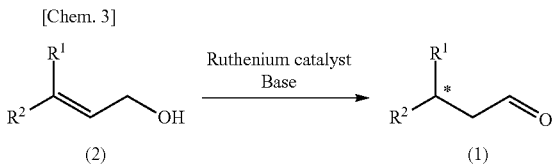

(in the formula (1) and the formula (2), $R^1$ and $R^2$ are each independently selected from the group consisting of an alkyl group having from 1 to 20 carbon atoms, which may have a substituent, an alkenyl group having from 2 to 20 carbon atoms, which may have a substituent, a 3- to 8-membered alicyclic group which may have a substituent, an aryl group having from 6 to 15 carbon atoms, which may have a substituent, and an aralkyl group having from 7 to 12 carbon atoms, which may have a substituent; $R^1$ and $R^2$ are groups different from each other; and * is an asymmetric carbon atom.

That is, the optically active aldehyde (1) is obtained by asymmetrically isomerizing the allyl alcohol (2) in the presence of a ruthenium complex and a base.

The allyl alcohol (2) represented by the following general formula (2), which is a starting material for producing the optically active aldehyde (1) in the present invention, is described.

[Chem. 4]

In the general formula (2), $R^1$ and $R^2$ are each independently selected from the group consisting of an alkyl group having from 1 to 20 carbon atoms, which may have a substituent, an alkenyl group having from 2 to 20 carbon atoms, which may have a substituent, a 3- to 8-membered alicyclic group which may have a substituent, an aryl group having from 6 to 15 carbon atoms, which may have a substituent, and an aralkyl group having from 7 to 12 carbon atoms, which may have a substituent, and $R^1$ and $R^2$ are groups different from each other.

The alkyl group having from 1 to 20 carbon atoms, which is represented by $R^1$ and $R^2$ in the general formula (2), is preferably an alkyl group having from 1 to 15 carbon atoms. Specifically, examples thereof include methyl group, ethyl group, n-propyl group, isopropyl group, n-butyl group, isobutyl group, sec-butyl group, tert-butyl group, n-pentyl group, isopentyl group, neopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group and the like.

The alkenyl group having from 2 to 20 carbon atoms, which is represented by $R^1$ and $R^2$ in the general formula (2), is preferably an alkenyl group having from 2 to 15 carbon atoms. Specifically, examples thereof include vinyl group, allyl group, 1-propenyl group, isopropenyl group, 1-butenyl group, 2-butenyl group, 3-butynyl group, 2-methylallyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, eicosenyl group, 4-methyl-3-pentenyl group, 4,8-dimethyl-3,7-nonadienyl group and the like.

The 3- to 8-membered alicyclic group represented by $R^1$ and $R^2$ in the general formula (2) is preferably a 5- to 7-membered alicyclic group. Specifically, examples thereof include cyclopropyl group, cyclobutyl group, cyclopentyl group, cyclohexyl group, cycloheptyl group, cyclooctyl group and the like.

The aryl group represented by $R^1$ and $R^2$ in the general formula (2) is preferably an aromatic monocyclic group, an aromatic polycyclic group or an aromatic condensed cyclic group, which has from 6 to 15 carbon atoms. Specifically, examples thereof include phenyl group, naphthyl group, anthryl group, phenanthryl group, indenyl group, biphenyl group and the like. Further, examples thereof also include a metallocenyl group such as ferrocenyl group.

The aralkyl group represented by $R^1$ and $R^2$ in the general formula (2) is preferably an aralkyl group having from 7 to 20 carbon atoms. Specifically, examples thereof include benzyl group, 1-phenylethyl group, 2-phenylethyl group and the like.

Here, the alkyl group having from 1 to 20 carbon atoms, the alkenyl group having from 2 to 20 carbon atoms, the 3- to 8-membered alicyclic group, the aryl group having from 6 to 15 carbon atoms and the aralkyl group having from 7 to 12 carbon atoms, which are represented by $R^1$ and $R^2$ in the above-mentioned general formula (2), may each have a substituent. Examples of the substituents include alkyl group, aryl group, aralkyl group, alicyclic group, halogen atom, hydroxyl group, alkoxy group, tri-substituted organosilyl group, oxycarbonyl group, acyl group, acyloxy group, substituted amino group, heterocyclic group, nitro group and the like.

Here, examples of the alkyl groups as substituents include, for example, alkyl groups having from 1 to 6 carbon atoms such as methyl group, ethyl group, n-propyl group, isopropyl group, sec-butyl group, tert-butyl group, pentyl group and hexyl group.

Examples of the aryl groups as substituents include, for example, aryl groups having from 6 to 14 carbon atoms such as phenyl group, α-naphthyl group, β-naphthyl group, anthryl group, phenanthryl group and biphenyl group.

Examples of the aralkyl groups as substituents include, for example, aralkyl groups having from 7 to 12 carbon atoms such as benzyl group, 1-phenylethyl group, 2-phenylethyl group, α-naphthylmethyl group and β-naphthylmethyl group.

Examples of the alicyclic groups as substituents include, for example, alicyclic groups having from 5 to 8 carbon atoms such as cyclopentyl group, cyclohexyl group, methylcyclohexyl group, cycloheptyl group and cyclooctyl group.

Examples of the halogen atoms as substituents include fluorine atom, chlorine atom, bromine atom, iodine atom and the like.

Examples of the alkoxy groups as substituents include, for example, alkoxy groups having from 1 to 4 carbon atoms such as methoxy group, ethoxy group, n-propoxy group, isopropoxy group, n-butoxy group, isobutoxy group, sec-butoxy group and tert-butoxy group.

Examples of the tri-substituted organosilyl groups as substituents are preferably trialkylsilyl groups such as trimethylsilyl group, triethylsilyl group, triisopropylsilyl group, dimethylisopropylsilyl group, diethylisopropylsilyl group, dimethyl(2,3-dimethyl-2-butyl)silyl group, tert-butyldimethylsilyl group or dimethylhexylsilyl group, and the carbon number of alkyl group moieties is preferably from 1 to 6.

Examples of the oxycarbonyl groups as substituents include alkoxycarbonyl groups having from 2 to 6 carbon atoms such as methoxycarbonyl group and ethoxycarbonyl group, and aryloxycarbonyl groups having from 6 to 11 carbon atoms such as phenoxycarbonyl group.

Examples of the acyl groups as substituents include acyl groups having from 1 to 8 carbon atoms such as formyl group, acetyl group, propionyl group, n-butyloyl group, isobutyloyl group and benzoyl group.

Examples of the acyloxy groups as substituents include acyloxy groups having from 1 to 8 carbon atoms such as formyloxy group, acyloxy group, propionyloxy group, n-butyloyloxy group, isobutyloyloxy group and benzoyloxy group.

Examples of the substituted amino groups as substituents include dialkylamino groups substituted with alkyl groups having from 1 to 12 carbon atoms, such as dimethylamino group, diethylamino group, diisopropylamino group and piperidyl group.

Examples of the heterocyclic groups as substituents include aliphatic heterocyclic groups and aromatic heterocyclic groups, and examples of the aliphatic heterocyclic groups include, for example, 3- to 8-membered, preferably 5- or 6-membered monocyclic, polycyclic or condensed cyclic aliphatic heterocyclic groups having from 2 to 14 carbon atoms and containing at least one, preferably from 1 to 3 hetero atoms. Examples of the hetero atoms include, for example, hetero atoms such as nitrogen atom, oxygen atom and sulfur atom.

Specific examples of the aliphatic heterocyclic groups include, for example, oxiranyl group, aziridinyl group, 2-oxopirrolidyl group, piperidyl group, piperazinyl group, morpholino group, tetrahydrofuryl group, tetrahydropyranyl group, tetrahydrothienyl group and the like.

On the other hand, examples of the aromatic heterocyclic groups include, for example, 5- to 8-membered, preferably 5- or 6-membered monocyclic, polycyclic or condensed cyclic aromatic heterocyclic (heteroaryl) groups containing at least one, preferably from 1 to 3 hetero atoms and having from 2 to 15 carbon atoms. Examples of the hetero atoms include, for example, hetero atoms such as nitrogen atom, oxygen atom and sulfur atom.

Specific examples of the aromatic heterocyclic groups include tetrazinyl group, furyl group, thienyl group, pyridyl group, pyridinyl group, pyrazinyl group, pyridazinyl group, imidazoyl group, oxazoyl group, thiazoyl group, benzofuryl group, benzothienyl group, quinolyl group, isoquinolyl group, quinoxalinyl group, phthalazinyl group, quinazolinyl group, naphthyridinyl group, cinnolinyl group, benzimidazoline group, benzoxazolyl group, benzothiazolyl group and the like.

Specifically, examples of the allyl alcohol represented by the general formula (2) in the present invention (hereinafter sometimes referred to as the "allyl alcohol (2)") include the following compounds.

Examples thereof include 3-methyl-2-pentenol, 3-methyl-2-hexenol, 3-methyl-2-heptenol, 3-methyl-2-octenol, 3-methyl-2-nonenol, 3-methyl-2-decenol, 3-ethyl-2-heptenol, 3-ethyl-2-octenol, 3-ethyl-2-nonenol, 3-ethyl-2-decenol, 3-phenyl-4-methyl-2-pentenol, 3-(4-methylphenyl)-4-methyl-2-pentenol, 3-(4-methoxyphenyl)-4-methyl-2-pentenol, 3-(4-chlorophenyl)-4-methyl-2-pentenol, 3-(2-naphthyl)-4-methyl-2-pentenol, 3-phenyl-3-cyclohexyl-2-propenol, 3-phenyl-2-pentenol, 3-phenyl-2-butenol, 3-trifluoromethyl-3-phenyl-2-propenol, 3-cyclohexyl-2-butenol, geraniol ((E)-3,7-dimethyl-2,6-octadien-1-ol), nerol ((Z)-3,7-dimethyl-2,6-octadien-1-ol), farnesol (3,7,1-trimethyl-2,6,10-dodecatrien-1-ol) and the like.

Each of these has a double bond in its molecule, so that there are geometrical isomers of an (E)-form and a (Z)-form. However, when used in the asymmetric isomerization reaction carried out in the present invention, the (E)-form and the (Z)-form are used alone.

In the method in the present invention, the optically active aldehyde represented by the general formula (1) is produced by asymmetrically isomerizing the allyl alcohol represented by the general formula (2) in the presence of the ruthenium complex and the base.

As the ruthenium catalyst that is used in the asymmetric isomerization reaction in the present invention, preferable examples thereof include a complex including ruthenium and a ligand. Preferably, the ligand is an asymmetric ligand, in which, however, constituent component other than the ligand may be an optically active form.

The asymmetric ligand to be used in the present invention may be any and every optically active compound having an optically active site and capable of being used as an asymmetric ligand. Examples of the asymmetric ligand include, for example, those described in Catalytic Asymmetric Synthesis (Wiley-VCH, 2000), Handbook of Enantioselective Catalysis with Transition Metal Complex (VCH, 1993), ASYMMETRIC CATALYSIS IN ORGANIC SYNTHESIS (John Wiley & Sons Inc. (1994)), WO 2005/070875, etc.

This is described more concretely. Examples of the asymmetric ligand for use in the present invention include, for example, a monodentate ligand, a bidentate ligand, a tridentate ligand, a quadridentate ligand, etc. For example, examples thereof include optically active phosphine compounds, optically active amine compounds, optically active alcohol compounds, optically active sulfur compounds, optically active carbene compounds, etc. Preferable examples thereof include optically active phosphine compounds.

As the optically active phosphine compounds, examples thereof include optically active bidentate phosphine ligands represented by the following general formula (5):

[Chem. 5]

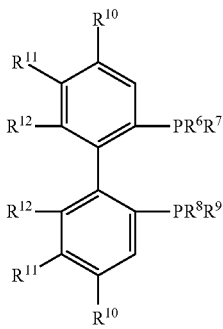

(5)

In the formula (5), $R^6$ to $R^9$ each independently represents an aromatic group which may have a substituent or a cycloalkyl group having from 3 to 10 carbon atoms or $R^6$ and $R^7$, and $R^8$ and $R^9$ each may form a hetero ring with the adjacent phosphorus atom; $R^{10}$ and $R^{11}$ each independently represents hydrogen atom, an alkyl group having from 1 to 5 carbon atoms, an alkoxy group having from 1 to 5 carbon atoms, a di($C_{1-5}$ alkyl)amino group, a 5- to 8-membered cyclic amino group or a halogen atom; $R^{12}$ represents an alkyl group having from 1 to 5 carbon atoms, an alkoxy group having from 1 to 5 carbon atoms, a di($C_{1-5}$ alkyl) amino group, a 5- to 8-membered cyclic amino group or a halogen atom; or $R^{10}$ and $R^{11}$, and $R^{11}$ and $R^{12}$ each may bond to each other to form a condensed benzene ring, a condensed substituted benzene ring, trimethylene group, tetramethylene group, pentamethylene group, methylenedioxy group, ethylenedioxy group or trimethylenedioxy group.

In the general formula (5), $R^6$ to $R^9$ each independently represents an aromatic group which may have a substituent or a cycloalkyl group having from 3 to 10 carbon atoms, or $R^6$ and $R^7$, and $R^8$ and $R^9$ each may form a hetero ring with the adjacent phosphorus atom.

In the aromatic group which may have a substituent, examples of the aromatic group include a hydrocarbon aromatic group such as phenyl group, naphthyl group and phenanthryl group; and a heterocyclic aromatic group such as pyrrolyl group, pyridyl group, pyrazyl group, quinolyl group, isoquinolyl group and imidazolyl group.

Here, specific examples of the substituent include, for example, an alkyl group having from 1 to 12 carbon atoms such as methyl group, ethyl group, n-propyl group, isopropyl group, n-butyl group, isobutyl group, sec-butyl group, tert-butyl group, n-pentyl group, isopentyl group, neopentyl group, hexyl group, heptyl group, octyl group, nonyl group, decyl group, undecyl group and dodecyl group; a lower alkoxy group having from 1 to 4 carbon atoms such as methoxy group, ethoxy group, n-propoxy group, isopropoxy group, n-butoxy group, isobutoxy group, sec-butoxy group and tert-butoxy group; an aryl group such as phenyl group, α-naphthyl group, β-naphthyl group and phenanthryl group; an aralkyl group having from 7 to 13 carbon atoms such as benzyl group. α-phenylethyl group, β-phenylethyl group, α-phenylpropyl group, β-phenylpropyl group, γ-phenylpropyl group and naphthylmethyl group; a tri-substituted organosilyl group, for example, a tri-$C_{1-6}$ alkylsilyl group such as trimethylsilyl group, triethylsilyl group, triisopropylsilyl group, dimethylisopropylsilyl group, diethylisopropylsilyl group, dimethyl(2,3-dimethyl-2-butyl)silyl group, tert-butyldimethylsilyl group and dimethylhexylsilyl group, a di-$C_{1-6}$ alkyl-$C_{6-18}$ arylsilyl group such as dimethylcumylsilyl group, a di-$C_{6-18}$ aryl-$C_{1-6}$ alkylsilyl group such as tert-butyldiphenylsilyl group and diphenylmethylsilyl group, a tri-$C_{6-18}$ arylsilyl group such as triphenylsilyl group, a tri-$C_{7-19}$ aralkylsilyl group such as tribenzylsilyl group and a tri-p-xylylsilyl group; a halogen atom such as fluorine, chlorine, bromine and iodine; a nitro group, etc.

Specific examples of the cycloalkyl group having from 3 to 10 carbon atoms, which may have a substituent, include cyclopentyl group, cyclobutyl group, cyclopentyl group, cyclohexyl group, cycloheptyl group, cyclooctyl group, cyclononyl group, cyclodecyl group and octahydronaphthyl group.

Here, specific examples of the substituent include, for example, an alkyl group having from 1 to 12 carbon atoms such as methyl group, ethyl group, n-propyl group, isopropyl group, n-butyl group, isobutyl group, sec-butyl group, tert-butyl group, n-pentyl group, isopentyl group, neopentyl group, hexyl group, heptyl group, octyl group, nonyl group, decyl group, undecyl group and dodecyl group; a lower alkoxy group having from 1 to 4 carbon atoms such as methoxy group, ethoxy group, n-propoxy group, isopropoxy group, n-butoxy group, isobutoxy group, sec-butoxy group and tert-butoxy group; an aryl group such as phenyl group, α-naphthyl group, β-naphthyl group and phenanthryl group; an aralkyl group having from 7 to 13 carbon atoms such as benzyl group, α-phenylethyl group, β-phenylethyl group, α-phenylpropyl group, β-phenylpropyl group, γ-phenylpropyl group and naphthylmethyl group; a tri-substituted organosilyl group, for example, a tri-$C_{1-6}$ alkylsilyl group such as trimethylsilyl group, triethylsilyl group, triisopropylsilyl group, dimethylisopropylsilyl group, diethylisopropylsilyl group, dimethyl(2,3-dimethyl-2-butyl)silyl group, tert-butyldimethylsilyl group and dimethylhexylsilyl group, a di-$C_{1-6}$ alkyl-$C_{6-18}$ arylsilyl group such as dimethylcumylsilyl group, a di-$C_{6-18}$ aryl-$C_{1-6}$ alkylsilyl group such as tert-butyldiphenylsilyl group and diphenylmethylsilyl group, a tri-$C_{6-18}$ arylsilyl group such as triphenylsilyl group, a tri-$C_{7-19}$ aralkylsilyl group such as tribenzylsilyl group and a tri-p-xylylsilyl group; a halogen atom such as fluorine, chlorine, bromine and iodine; a nitro group, etc.

Specific examples of the hetero ring to be formed by $R^6$ and $R^7$, or $R^8$ and $R^9$ each bonding to the adjacent phosphorus atom include phosphole, tetrahydrophosphole and phosphorinane. The hetero ring may have, as substituents, from 1 to 4 functional groups inert to the reaction in the present invention. Examples of the substituent include, for example, an alkyl group having from 1 to 4 carbon atoms, an alkoxy group having from 1 to 4 carbon atoms and a halogen atom.

In the general formula (5), $R^{10}$ and $R^{11}$ each independently represents hydrogen atom, an alkyl group having from 1 to 5 carbon atoms, an alkoxy group having from 1 to 5 carbon atoms, a di($C_{1-5}$ alkyl)amino group, a 5- to 8-membered cyclic amino group or a halogen atom.

Specific examples of the alkyl group having from 1 to 5 carbon atoms, which is represented by $R^{10}$ and $R^{11}$, include, for example, methyl group, ethyl group, n-propyl group, isopropyl group, n-butyl group, isobutyl group, sec-butyl group, tert-butyl group and a pentyl group.

Specific examples of the alkoxy group having from 1 to 5 carbon atoms, which is represented by $R^{10}$ and $R^{11}$, include, for example, methoxy group, ethoxy group, n-propoxy group, isopropoxy group, n-butoxy group, isobutoxy group, sec-butoxy group, tert-butoxy group and pentoxy group.

Specific examples of the di($C_{1-5}$ alky)amino group which is represented by $R^{10}$ and $R^{11}$ include dimethylamino group, diethylamino group, di-n-propylamino group, diisopropylamino group, di-n-butylamino group, di-isobutylamino group, di-sec-butylamino group, di-tert-butylamino group and dipentylamino group.

Specific examples of the 5- to 8-membered cyclic amino group which is represented by $R^{10}$ and $R^{11}$ include pyrrolidino group and piperidino group.

Specific examples of the halogen atom which is represented by $R^{10}$ and $R^{11}$ include fluorine atom, chlorine atom, bromine atom and iodine atom.

Of those, examples of preferred $R^{10}$ and $R^{11}$ include hydrogen atom; an alkyl group having from 1 to 4 carbon atoms such as methyl group, ethyl group, propyl group, isopropyl group, n-butyl group, tert-butyl group and trifluoromethyl group; an alkoxy group such as methoxy group, ethoxy group, n-propoxy group, isopropoxy group, n-butoxy group and tert-butoxy group; a dialkylamino group such as dimethylamino group and diethylamino group; a 5- to 8-membered cyclic amino group such as pyrrolidino group and piperidino group, etc.

Examples of more preferred $R^{10}$ and $R^{11}$ include hydrogen atom and methoxy group.

In the general formula (5), $R^{12}$ each independently represents an alkyl group having from 1 to 5 carbon atoms, an alkoxy group having from 1 to 5 carbon atoms, a di($C_{1-5}$ alkyl)amino group, a 5- to 8-membered cyclic amino group or a halogen atom.

Specific examples of the alkyl group having from 1 to 5 carbon atoms, which is represented by $R^{12}$, include, for example, methyl group, ethyl group, n-propyl group, isopropyl group, n-butyl group, isobutyl group, sec-butyl group, tert-butyl group and a pentyl group.

Specific examples of the alkoxy group having from 1 to 5 carbon atoms, which is represented by $R^{12}$, include, for example, methoxy group, ethoxy group, n-propoxy group, isopropoxy group, n-butoxy group, isobutoxy group, sec-butoxy group, tert-butoxy group and pentoxy group.

Specific examples of the di($C_{1-5}$ alky)amino group which is represented by $R^{12}$ include dimethylamino group, diethylamino group, di-n-propylamino group, diisopropylamino group, di-n-butylamino group, di-isobutylamino group, di-sec-butylamino group, di-tert-butylamino group and dipentylamino group.

Specific examples of the 5- to 8-membered cyclic amino group which is represented by $R^{12}$ include pyrrolidino group and piperidino group.

Specific examples of the halogen atom which is represented by $R^{12}$ include fluorine, chlorine, bromine and iodine.

Of those, examples of preferred $R^{12}$ include an alkyl group having from 1 to 4 carbon atoms such as methyl group, ethyl group, propyl group, isopropyl group, n-butyl group, tert-butyl group and trifluoromethyl group; an alkoxy group such as methoxy group, ethoxy group, n-propoxy group, isopropoxy group, n-butoxy group and tert-butoxy group; a dialkylamino group such as dimethylamino group and diethylamino group; a 5- to 8-membered cyclic amino group such as pyrrolidino group and piperidino group, etc.

Examples of more preferred $R^{12}$ include methyl group and methoxy group.

In the general formula (5), $R^{10}$ and $R^{11}$, and $R^{11}$ and $R^{12}$ each may bond to each other to form a condensed benzene ring, a condensed substituted benzene ring, trimethylene group, tetramethylene group, pentamethylene group, methylenedioxy group, ethylenedioxy group or trimethylenedioxy group. Of those, preferred examples thereof include a condensed benzene ring, a condensed substituted benzene ring, trimethylene group, tetramethylene group, pentamethylene group, methylenedioxy group, ethylenedioxy group or trimethylenedioxy group that is formed by $R^{11}$ and $R^{12}$ bonding to each other. More preferred examples thereof include a condensed benzene ring, a condensed substituted benzene ring, tetramethylene group, methylenedioxy group, methylenedioxy group or ethylenedioxy group that is formed by $R^{11}$ and $R^{12}$ bonding to each other.

The condensed benzene ring, the condensed substituted benzene ring, the trimethylene group, the tetramethylene group, the pentamethylene group, the methylenedioxy group, the ethylenedioxy group or the trimethylenedioxy group may have, as the substituent, a functional group inert to asymmetric synthesis reaction, and preferably the number of the substituents is within a range of from 0 to 4. Examples of the substituent include, for example, an alkyl group having from 1 to 4 carbon atoms such as methyl group, ethyl group, n-propyl group, isopropyl group, n-butyl group, isobutyl group, sec-butyl group and tert-butyl group; hydroxyl group; an alkoxy group having from 1 to 4 carbon atoms such as methoxy group, ethoxy group, n-propoxy group, isopropoxy group, n-butoxy group, isobutoxy group, sec-butoxy group and tert-butoxy group; a halogen atom such as fluorine, chlorine, bromine, iodine, etc.

Examples of the optically active bidentate phosphine ligand preferably used in the general formula (5) include, for example, a tertiary phosphine described in JP-A 61-63690 and JP-A 62-265293, and as concrete examples thereof, the following examples are exemplified: 2,2'-bis(diphenylphosphino)-1,1'-binaphthyl (BINAP), 2,2'-bis(di(p-tolylphosphino)-1,1'-binaphthyl [p-Tol-BINAP], 2,2'-bis(di(3,5-xylyl)phosphino)-1,1'-binaphthyl(DM-BINAP), 2,2'-bis(di(3, 5-di-tert-butylphenyl)phosphino)-1,1'-binaphthyl (T-Bu-2-BINAP), 2,2'-bis[di(4-methoxy-3,5-dimethylphenyl) phosphino]-1,1'-binaphthyl (DMM-BINAP), 2,2'-bis (dicyclohexylphosphino)-1,1'-binaphthyl (Cy-BINAP) and 2,2'-bis(dicyclopentylphosphino)-1,1'-binaphthyl (Cp-BINAP).

Further, examples of the optically active bidentate phosphine ligand preferably used in the general formula (5) include, for example, a tertiary phosphine described in JP-A 4-139140, and concrete examples thereof include: 2,2'-bis (diphenylphosphino)-5,5',6,6',7,7',8,8'-octahydrobinaphthyl ($H_8$-BINAP), 2,2'-bis(di-p-tolylphosphino)-5,5',6,6',7,7',8, 8'-octahydrobinaphthyl (p-Tol-$H_8$-BINAP), 2,2'-bis(di-(3,5-xylyl)phosphino)-5,5',6,6',7,7',8,8'-octahydrobinaphthyl (DM-$H_8$-BINAP), and 2,2'-bis(di-(4-methoxy-3,5-dimehtylphenyl)phosphino)-5,5',6,6',7,7',8,8'-octahydrobinaphthyl (DMM-$H_8$-BINAP).

Still further, examples of the optically active bidentate phosphine ligand preferably used in the general formula (5) include, for example, a tertiary phosphine described in JP-A 11-269185, and concrete examples thereof include: ((5,6), (5',6')-bis(methylenedioxy)biphenyl-2,2'-diyl)bis(diphenylphosphine) (SEGPHOS), ((5,6),(5',6')-bis(methylenedioxy) biphenyl-2,2'-diyl)bis(di-p-tolylphosphine) (p-Tol-SEGPHOS), ((5,6),(5',6')-bis(methylenedioxy)biphenyl-2, 2'-diyl)bis(di-3,5-xylylphosphine) (DM-SEGPHOS), ((5,6), (5',6')-bis(methylenedioxy)biphenyl-2,2'-diyl)bis(di-4-methoxy-3,5-dimehtylphenylphosphine) (DMM-SEGPHOS), ((5,6),(5',6')-bis(methylencdioxy)biphenyl-2, 2'-diyl)bis(di-4-methoxy-3,5-di-tert-butylphenylphosphine) (DTBM-SEGPHOS), ((5,6),(5',6')-bis(methylenedioxy)biphenyl-2,2'-diyl)bis(dicyclohexylphosphine) (Cy-SEGPHOS).

Other than the above-mentioned optically active bidentate phosphine ligands, the following optically active bidentate phosphine ligands are mentioned as those corresponding to the general formula (5): 2,2'-dimethyl-6,6'-bis(diphenylphosphino)-1,1'-biphenyl (BIPHEMP), 2,2'-dimethyl-6,6'-bis(di-p-tolylphosphino)-1,1'-biphenyl (p-Tol-BIPHEMP), 2,2'-dimethyl-6,6'-bis(di-3,5-xylylphosphino)-1,1'-biphenyl (DM-BIPHEMP), 2,2'-dimethyl-6,6'-bis(di-4-methoxy-3,5-dimethylphenylphosphino)-1,1'-biphenyl (DMM-BIPHEMP), 2,2'-dimethyl-6,6'-bis(di-4-t-butoxy-3,5-dimethylphenylphosphino)-1,1'-biphenyl (DTBM-BIPHEMP), 2,2'-dimethyl-6,6'-bis(dicyclohexylphosphino)-1,1'-biphenyl (Cy-BIPHEMP), 2,2'-dimethoxy-6,6'-bis(diphenylphosphino)-1,1'-biphenyl (MeO-BIPHEMP), 2,2'-dimethoxy-6,6'-bis(di-p-tolylphosphino)-1,1'-biphenyl (p-Tol-MeO-BIPHEMP), 2,2'-dimethoxy-6,6'-bis(di-3,5-xylylphosphino)-1,1'-biphenyl (DM-MeOBIPHEMP), 2,2'-dimethoxy-6,6'-bis(di-4-methoxy-3,5-dimethylphenylphosphino)-1,1'-biphenyl (DMM-MeO-BIPHEMP), 2,2'-dimethoxy-6,6'-bis(di-4-t-butoxy-3,5-dimethylphenylphosphino)-1,1'-biphenyl (DTBM-MeO-BIPHEMP), 2,2'-dimethoxy-6,6'-bis(dicyclohexylphosphino)-1,1'-biphenyl (Cy-MeO-BIPHEMP), 2,2'-dimethyl-3,3'-dichloro-4,4'-dimethyl-6,6'-bis(di-p-tolylphosphino)-1,1'-biphenyl (p-Tol-CM-BIPHEMP), 2,2'-dimethyl-3,3'-dichloro-4,4'-dimethyl-6,6'-bis(di-3,5-xylylphosphino)-1,1'-biphenyl (DM-CM-BIPHEMP), 2,2'-dimethyl-3,3'-dichloro-4,4'-dimethyl-6,6'-bis(di-4-methoxy-3,5-dimethylphenylphosphino)-1,1'-biphenyl (DMM-CM-BIPHEMP).

In the present invention, a ruthenium complex containing the above-mentioned optically active bidentate phosphine ligand and ruthenium is used for asymmetric isomerization reaction. As the optically active ruthenium complex for the asymmetric isomerization reaction, for example, preferred examples thereof include the compounds represented by the following general formula (3):

$$[Ru_mL_nW_pU_q]_rZ_s \qquad (3)$$

In the formula, L represents an optically active phosphine ligand; W represents hydrogen atom, a halogen atom, an acyloxy group, an aryl group, a diene or an anion; U represents hydrogen atom, a halogen atom, an acyloxy group, an aryl group, a diene, an anion or a ligand other than L; Z represents an anion, amine or an optically active nitrogen-containing compound; m, n and r each independently indicates an integer of from 1 to 5; p, q and s each independently indicates an integer of from 0 to 5, and p+q+s is 1 or more.

In the general formula (3), examples of the ligand represented by L include the above-mentioned optically active bidentate phosphine ligand represented.

In the general formula (3), W represents hydrogen atom, a halogen atom, an acyloxy group, an aryl group, a diene or an anion.

Examples of the halogen atom represented by W in the general formula (3) include, for example, fluorine atom, chlorine atom, bromine atom and iodine atom.

Examples of the acyloxy group represented by W in the general formula (3) include, for example, formyloxy group, acetoxy group, propionyloxy group, butyloxy group, benzoyloxy group, etc.

Examples of the aryl group represented by W in the general formula (3) include, for example, aromatic monocyclic or polycyclic groups, such as phenyl group, naphthyl group, anthranyl group, phenanthryl group, indenyl group, mesityl group, dibenzyl group, etc.

Examples of the diene represented by W in the general formula (3) include, for example, butadiene, cyclooctadiene (cod), norbornadiene (nod), etc.

Examples of the anion represented by W in the general formula (3) include, for example, nitrate ion, nitrite ion, sulfate ion, sulfite ion, sulfonate ion (methanesulfonate ion, benzenesulfonate ion, p-toluenesulfonate ion, camphorsulfonate ion, trifluoromethanesulfonate ion, etc.), sulfamate ion, carbonate ion, hydroxide ion, carboxylate ion (formate ion, acetate ion, propionate ion, gluconate ion, oleate ion, oxalate ion, benzoate ion, phthalate ion, trifluoroacetate ion, etc.), sulfide ion, thiocyanate ion, phosphate ion, pyrophosphate ion, oxide ion, phosphide ion, chlorate ion, perchlorate ion, iodate ion, hexafluorosilicate ion, cyanide ion, borate ion, metaborate ion, borofluoride ion, etc.

In the general formula (3), U represents hydrogen atom, a halogen atom, an acyloxy group, an aryl group, a diene, an anion or a ligand other than L.

Examples of the halogen atom represented by U in the general formula (3) include, for example, fluorine atom, chlorine atom, bromine atom and iodine atom.

Examples of the acyloxy group represented by U in the general formula (3) include, for example, formyloxy group, acetoxy group, propionyloxy group, butyloxy group, benzoyloxy group, etc.

Examples of the aryl group represented by U in the general formula (3) include, for example, aromatic monocyclic or polycyclic groups, such as phenyl group, naphthyl group, anthranyl group, phenanthryl group, indenyl group, mesityl group, dibenzyl group, etc.

Examples of the diene represented by U in the general formula (3) include, for example, butadiene, cyclooctadiene (cod), norbornadiene (nod), etc.

Examples of the anion represented by U in the general formula (3) include, for example, nitrate ion, nitrite ion, sulfate ion, sulfite ion, sulfonate ion (methanesulfonate ion, benzenesulfonate ion, p-toluenesulfonate ion, camphorsulfonate ion, trifluoromethanesulfonate ion, etc.), sulfamate ion, carbonate ion, hydroxide ion, carboxylate ion (formate ion, acetate ion, propionate ion, gluconate ion, oleate ion, oxalate ion, benzoate ion, phthalate ion, trifluoroacetate ion, etc.), sulfide ion, thiocyanate ion, phosphate ion, pyrophosphate ion, oxide ion, phosphide ion, chlorate ion, perchlorate ion, iodate ion, hexafluorosilicate ion, cyanide ion, borate ion, metaborate ion, borofluoride ion, etc.

Examples of the ligand except L, which is represented by U in the general formula (3), include, for example, N,N-dimethylformamide (DMF), acetone, chloroform, a nitrile (acetonitrile, benzonitrile, etc.), a cyanide (methylisocyanide, phenylisocyanide, etc.), an aromatic compound (benzene, p-cymene, 1,3,5-trimethylbenzene (mesitylene), hexamethylbenzene, etc.), an olefin (ethylene, propylene, cycloolefin, etc.), a phosphorus compound (phosphane compounds such as triphenyl phosphine, tritolyl phosphine, trimethyl phosphine, triethyl phosphine, methyldiphenyl phosphine, dimethylphenyl phosphine, diphenylphosphinomethane (dppm), diphenylphosphinoethane (dppe), diphenylphosphinopropane (dppp), diphenylphosphinobutane (dppb) and diphenylphosphinoferrocene (dppf), phosphite compounds such as trimethyl phosphite, triethyl phosphite and triphenyl phosphite), an amine compound (ammonia; an aliphatic amine such as methylamine, ethylamine, n-propylamine, isopropylamine, n-butylamine, s-butylamine, tert-butylamine and cyclohexylamine; an aromatic amine such as aniline and dimethylaniline; a nitrogen-containing aromatic heterocyclic compound such as pyridine (py) and dimethylaminopyridine; a nitrogen-containing aliphatic heterocyclic compound such as pyrrolidine and piperazine; a diamine such as ethylenediamine (en), propylenediamine, triethylenediamine, tetramethylethylenediamine (TMEDA), bipyridine (bpy) and phenanthroline (phen)), a sulfur compound (dimethyl sulfide, diethyl sulfide, dipropyl sulfide, dibutyl sulfide, etc.), etc.

In the general formula (3), Z represents an anion, amine or an optically active nitrogen-containing compound.

Examples of the anion represented by Z in the general formula (3) include, for example, nitrate ion, nitrite ion, sulfate ion, sulfite ion, sulfonate ion (methanesulfonate ion, benzenesulfonate ion, p-toluenesulfonate ion, camphorsulfonate ion, trifluoromethanesulfonate ion, etc.), sulfamate ion, carbonate ion, hydroxide ion, carboxylate ion (formate ion, acetate ion, propionate ion, gluconate ion, oleate ion, oxalate ion, benzoate ion, phthalate ion, trifluoroacetate ion, etc.), sulfide ion, thiocyanate ion, phosphate ion, pyrophosphate ion, oxide ion, phosphide ion, chlorate ion, perchlorate ion, iodate ion, hexafluorosilicate ion, cyanide ion, borate ion, metaborate ion, borofluoride ion, etc.

Examples of the amine represented by Z in the general formula (3) include, for example, an aliphatic amine such as methylamine, ethylamine, n-propylamine, isopropylamine, n-butylamine, s-butylamine, tert-butylamine and cyclohexylamine; an aromatic amine such as aniline and dimethylaniline; a nitrogen-containing aromatic heterocyclic compound such as pyridine (py) and dimethylaminopyridine; a nitrogen-containing aliphatic heterocyclic compound such as pyrrolidine and piperazine; a diamine such as ethylenediamine (en), propylenediamine, triethylenediamine, tetramethylethylenediamine (TMEDA), bipyridine (bpy) and phenanthroline (phen); a sulfur compound (dimethyl sulfide, diethyl sulfide, dipropyl sulfide, dibutyl sulfide, etc.), etc.

Examples of the optically active nitrogen-containing compound represented by Z in the general formula (3) include an optically active diamine compound represented by the following general formula (6).

[Chem. 6]

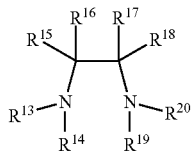

(6)

$R^{13}$, $R^{14}$, $R^{19}$ and $R^{20}$ each independently represents hydrogen atom, a saturated hydrocarbon group, unsaturated hydrocarbon group, an aryl group, an alaryl group, an urethane group, a sulfonyl group, etc.; $R^{15}$, $R^{16}$, $R^{17}$ and $R^{18}$ may be the same or different group, respectively, and each independently represents hydrogen atom, an alkyl group, an aromatic monocyclic, an aromatic polycyclic group, a saturated or unsaturated hydrocarbon group, a cyclic hydrocarbon group, etc., in which the carbon atom to which $R^{15}$, $R^{16}$, $R^{17}$ and $R^{18}$ bond is an asymmetric center.

For example, the following optically active diamine compounds are exemplified: 1,2-diphenylethylenediamine, 1,2-cyclohexanediamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl) ethylenediamine, 1-benzyl-2,2-di(p-methoxyphenyl) ethylenediamine, 1-methyl-2,2-dinaphthylethylenediamine, 1-isobutyl-2,2-dinaphthylethylenediamine, 1-isopropyl-2,2-dinaphthylethylenediamine, 2-methylamino-1-phenylethylamine, 2-ethylamino-1-phenylethylamine, 2-n-propylamino-1-phenylethylamine, 2-i-propylamino-1-phenylethylamine, 2-n-butylamino-1-phenylethylamine, 2-tert-butylamino-1-phenylethylamine, 2-cyclohexylamino-1-phenylethylamine, 2-benzylamino-1-phenylethylamine, 2-dimethylamino-1-phenylethylamine, 2-diethylamino-1-phenylethylamine, 2-di-n-propylamino-1-phenylethylamine, 2-di-i-propylamino-1-phenylethylamine, 2-di-n-butylamino-1-phenylethylamine, 2-di-tert-butylamino-1-phenylethylamine, 2-pyrrolidinyl-1-phenylethylamine, 2-piperidino-1-phenylethylamine, etc, which are optically active.

Further, as the optically active diamine compounds usable in the present invention, examples thereof include optically active diamine compounds described in JP-A 8-225466, JP-A 11-189600, JP-A 2001-58999, JP-A 2002-284790, JP-A 2005-68113, WO 2002/055477, WO 2004/007506, etc.

As preferred examples of the ruthenium complex represented by the general formula (3), the following ones are mentioned. Specifically, the following compounds are mentioned.

(i) W is chlorine atom, bromine atom or iodine atom, Z is a trialkylamine, m=p=s=1, n=r=2, q=0; (ii) W is chlorine atom, bromine atom or iodine atom. Z is pyridyl group or a ring-substituted pyridyl group, m=n=r=s=1, p=2, q=0; (iii) W is an acyloxy group, m=n=r=1, p=2, q=s=0; (iv) W is chlorine atom, bromine atom or iodine atom, Z is dimethylformamide or dimethylacetamide, m=n=r=1, p=2, q=0, and s is an integer of from 0 to 4; (v) W is chlorine atom, bromine atom or iodine atom, U is chlorine atom, bromine atom or iodine atom, Z is a dialkylammonium ion, m=n=p=2, q=3, r=s=1; (vi) W is chlorine atom, bromine atom or iodine atom. U is a neutral ligand of an aromatic compound or an olefin, Z is chlorine atom, bromine atom, iodine atom, $I_3$, $BF_4$, $ClO_4$, OTf, $PF_6$, $SbF_6$ or $BPh_4$, m=n=p=q=r=s=1; (vii) Z is $BF_4$, $ClO_4$, OTf, $PF_6$, $SbF_6$ or $BPh_4$, m=n=r=1, p=q=0, s=2; (viii) W and U may be the same or different, representing hydrogen atom, chlorine atom, bromine atom, iodine atom, a carboxyl group or any other anion group, Z is a diamine compound, m=n=p=q=r=s=1; (ix) W is hydrogen atom, U is chlorine atom, bromine atom or iodine atom, m=p=q=r=1, n=2, s=0; (x) W is hydrogen atom, Z is $BF_4$, $ClO_4$, OTf, $PF_6$, $SbF_6$ or $BPh_4$, m=n=p=r=s=1, q=0; (xi) W is chlorine atom, bromine atom or iodine atom, U is a monovalent phosphine ligand, Z is chlorine atom, bromine atom or iodine atom, m=n=p=q=1, r=z=2; (xii) W and U are the same or different, each representing chlorine atom, bromine atom or iodine atom, m=n=p=q=r=1, s=0.

The production method for the ruthenium phosphine complex (3) is not specifically defined. For example, the complex may be produced according to the method to be mentioned below or according to a method similar thereto. In the formulae of the transition metal phosphine complexes to be shown below, cod means 1,5-cyclooctadiene, nbd means norbornadiene, Ph means phenyl group, Ac means acetyl group, acac means acetylacetonate, dmf means dimethylformamide, en means ethylenediamine, DPEN means 1,2-diphenylethylenediamine, DAIPEN means 1,1-di(p-methoxyphenyl)-2-isopropylethylenediamine, MAE means methylaminoethylamine, EAE means ethylaminoethylamine, MAPE means 2-methylamino-1-phenylethylamine, EAPE means 2-ethylamino-1-phenylethylamine, DMAPE means 2-dimethylamino-1-phenylethylamine, DEAPE means 2-diethylamino-1-phenylethylamine, DBAE means di-n-butylaminoethylamine, DBAPE means 2-di-n-butylamino-1-phenylethylamine.

Ruthenium Complex:

As a method for producing a ruthenium complex, for example, the complex can be produced by heating and refluxing [(1,5-cyclooctadiene)dichlororuthenium] ([Ru(cod)Cl$_2$]$_n$) and an optically active bidentate phosphine ligand, in an organic solvent in the presence of a trialkylamine, according to the description in literature (J. Chem. Soc., Chem. Commun., p. 922, 1985). In addition, the complex can also be produced by heating and refluxing bis[dichloro(benzene)ruthenium] ([Ru(benzene)Cl$_2$]$_2$) and an optically active bidentate phosphine ligand, in an organic solvent in the presence of a dialkylamine, according to the method described in JP-A 11-269185.

Further, the complex can be produced by heating and stirring bis[diiodo(para-cymene)ruthenium]([Ru(p-cymene)I$_2$]$_2$) and an optically active bidentate phosphine ligand in an organic solvent according to the method described in literature (J. Chem. Soc., Chem. Commun., p. 1208, 1989). Further, the complex can be synthetized by reacting Ru$_2$Cl$_4$(L)$_2$NEt$_3$, which is obtained according to the method in literature (J. Chem. Soc., Chem. Commun., p. 992, 1985) and a diamine compound in an organic solvent, according to the method described in JP-A 11-189600.

As specific examples of the ruthenium complex, for example, the following are mentioned.

Ru(OAc)$_2$(L), Ru(OCOCF$_3$)$_2$(L), Ru$_2$Cl$_4$(L)$_2$NEt$_3$, [RuCl$_2$(L)(dmf)$_n$], RuHCl(L), RuHBr(L), RuHI(L) [{RuCl(L)}$_2$(μ-Cl)$_3$][Me$_2$NH$_2$], [{RuBr(L)}$_2$(μ-Br)$_3$][Me$_2$NH$_2$], [{RuI(L)}$_2$(μ-I)$_3$][Me$_2$NH$_2$], [{RuCl(L)}$_2$(μ-Cl)$_3$][Me$_2$NH$_2$], [{RuBr(L)}$_2$(μ-Br)$_3$][Me$_2$NH$_2$], [{RuBr(L)}$_2$(μ-I)$_3$][Me$_2$NH$_2$], [RuCl[PPh$_3$](L)]$_2$(μ-Cl)$_2$, [RuBr[PPh$_3$](L)]$_2$(μ-Br)$_2$, [RuI[PPh$_3$](L)]$_2$(μ-I)$_2$, RuCl$_2$(L), RuBr$_2$(L), RuI$_2$(L), [RuCl$_2$(L)](dmf)$_n$, RuCl$_2$(L)(pyridine)$_2$, RuBr$_2$(L)(pyridine)$_2$, RuI$_2$(L)(pyridine)$_2$, RuCl$_2$(L)(2,2'-dipyridine), RuBr$_2$(L)(2,2'-dipyridine), RuI$_2$(L)(2,2'-dipyridine), [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [RuI(p-cymene)(L)]I$_3$, [Ru(L)](OTf)$_2$, [Ru(L)](BF$_4$)$_2$, [Ru(L)](ClO$_4$)$_2$, [Ru(L)](SbF$_6$)$_2$, [Ru(L)](PF$_6$)$_2$, [Ru(L)](BPh$_4$)$_2$, [RuCl$_2$(L)](en), [RuBr$_2$(L)](en), [RuI$_2$(L)](en), [RuH$_2$(L)](en), [RuCl$_2$(L)](DPEN), [RuBr$_2$(L)](DPEN), [RuI$_2$(L)](DPEN), [RuH$_2$(L)](DPEN), [RuCl$_2$(L)](DAIPEN), [RuBr$_2$(L)](DAIPEN), [RuI$_2$(L)](DAIPEN), [RuH$_2$(L)](DAIPEN), [RuCl$_2$(L)](MAE), [RuBr$_2$(L)](MAE), [RuI$_2$(L)](MAE), [RuH$_2$(L)](MAE), [RuCl$_2$(L)](EAE), [RuBr$_2$(L)](EAE), [RuI$_2$(L)](EAE), [RuH$_2$(L)](EAE), [RuCl$_2$(L)](MAPE), [RuBr$_2$(L)](MAPE), [RuI$_2$(L)](MAPE), [RuH$_2$(L)](MAPE), [RuCl$_2$(L)](DMAPE), [RuBr$_2$(L)](DMAPE), [RuI$_2$(L)](DMAPE), [RuH$_2$(L)](DMAPE), [RuCl$_2$(L)](DBAE), [RuBr$_2$(L)](DBAE), [RuI$_2$(L)](DBAE), [RuH$_2$(L)](DBAE), [RuCl$_2$(L)](DBAPE), [RuBr$_2$(L)](DBAPE), [RuI$_2$(L)](DBAPE), [RuH$_2$(L)](DBAPE), etc.

More preferred catalysts for the asymmetric isomerization in the present invention are complexes containing ruthenium and an optically active bidentate phosphine ligand. Most preferred are the following:

Ru$_2$Cl$_4$(L)$_2$NEt$_3$, [RuCl$_2$(L)(dmf)$_n$], [{RuCl(L)}$_2$(μ-Cl)$_3$][Me$_2$NH$_2$], [{RuBr(L)}$_2$(μ-Br)$_3$][Me$_2$NH$_2$], [{RuI(L)}$_2$(μ-I)$_3$][Me$_2$NH$_2$], [{RuCl(L)}$_2$(μ-Cl)$_3$][Me$_2$NH$_2$], [{RuBr(L)}$_2$(μ-Br)$_3$][Me$_2$NH$_2$], [{RuBr(L)}$_2$(μ-I)$_3$][Me$_2$NH$_2$], [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)], [RuI(p-cymene)(L)]I$_3$, [RuCl$_2$(L)](MAE), [RuBr$_2$(L)](MAE), [RuI$_2$(L)](MAE), [RuH$_2$(L)](MAE), [RuCl$_2$(L)](EAE), [RuBr$_2$(L)](EAE), [RuI$_2$(L)](EAE), [RuH$_2$(L)](EAE), [RuCl$_2$(L)](MAPE), [RuBr$_2$(L)](MAPE), [RuI$_2$(L)](MAPE), [RuH$_2$(L)](MAPE), [RuCl$_2$(L)](DMAPE), [RuBr$_2$(L)](DMAPE), [RuI$_2$(L)](DMAPE), [RuH$_2$(L)](DMAPE), [RuCl$_2$(L)](DBAE), [RuBr$_2$(L)](DBAE), [RuI$_2$(L)](DBAE), [RuH$_2$(L)](DBAE), [RuCl$_2$(L)](DBAPE), [RuBr$_2$(L)](DBAPE), [RuI$_2$(L)](DBAPE), [RuH$_2$(L)](DBAPE), etc.

As the base for use in the present invention, for example, salts represented by the following formula (8) is preferably used.

$$M'Z' \qquad (8)$$

In the formula, M' represents a metal of Li, Na or K, and Z' represents a halogen atom of Cl, Br or I.

As the salt represented by the general formula (8), concretely, for example, preferred here is use of metal salts such as LiCl, LiBr, LiI, NaCl, NaBr, NaI, KCl, KBr or KI. Further, ammonium salts such as (Bn)Et$_3$NCl, (Bn)Et$_3$NBr, (Bn)Et$_1$NI or the like may be selected; and phsohonium salts such as BuPh$_3$PCl, BuPh$_3$PBr, BuPh$_3$PI, (C$_6$H$_{13}$)Ph$_3$PBr, BrPPh$_3$(CH$_2$)$_4$PPh$_3$Br or the like may be selected to realize high selectivity (Bn is benzyl group, Et is ethyl group, Ph is phenyl group, Bu is butyl group).

As the optically active bidentate phosphine ligand for use in the present invention, there are cases of an (S)-form and an (R)-form, and any of these may be selected in accordance with the absolute configuration of the intended optically active aldehyde (1). Specifically, when (E)-3-phenyl-4-methyl-2-pentenol is used as the substance and, for example, when Tol-BINAP is used as the ligand, then an (S)-form of Tol-BINAP may be used for obtaining an (R)-form of optically active 3-phenyl-4-methylpentanol, and an (R)-form of Tol-BINAP may be used for obtaining an (S)-form of optically active 3-phenyl-4-methylpentanol. On the other hand, when (Z)-form thereof is used as the substance, an (R)-form of Tol-BINAP may be used for obtaining an (S)-form of optically active 3-phenyl-4-methylpentanol and an (S)-form of Tol-BINAP may be used for obtaining an (R)-form of optically active 3-phenyl-4-methylpentanol.

Further, in the present invention, an optically active nitrogen compound is used in combination with the optically active bidentate phosphine ligand. As the optically active nitrogen compound, there are cases of an (S)-form and an (R)-form, and any of these may be selected in accordance with the absolute configuration of the intended optically active aldehyde (1).

Specifically, when (E)-3-phenyl-4-methyl-2-pentenol is used as the substance and, for example, when Tol-BINAP and DBAPE are used as the ligand, then an (S)-form of Tol-BINAP and (R)-form of DBAPE may be used for obtaining an (R)-form of optically active 3-phenyl-4-methylpentanol, and an (R)-form of Tol-BINAP and (S)-form of DBAPE may be used for obtaining an (S)-form of optically active 3-phenyl-4-methylpentanol. On the other hand, when (Z)-form thereof is used as the substance, an (R)-form of Tol-BINAP and (S)-form of DBAPE may be used for obtaining an (S)-form of optically active 3-phenyl-4-methylpentanol and an (S)-form of Tol-BINAP and (R)-form of DBAPE may be used for obtaining an (R)-form of optically active 3-phenyl-4-methylpentanol.

The amount of the transition metal-optically active phosphine complex to be used is preferably from about 1/100 to 1/50000 mol relative to allyl alcohol (2).

The amount of the base to be added is preferably from 0.5 to 100 equivalents, more preferably from 2 to 40 equivalents relative to the transition metal-optically active phosphine complex.

The reaction solvent may be any one capable of solubilizing the asymmetric hydrogenation raw material and the catalyst system. For example, usable examples thereof include aromatic hydrocarbon solvents such as toluene and xylene; aliphatic hydrocarbon solvents such as pentane and hexane; halogen-containing hydrocarbon solvents such as methylene chloride; ether solvents such as diethyl ether, diisopropyl ether, diethylene glycol dimethyl ether, tetrahydrofuran and 1,3-dioxolane; alcohol solvents such as methanol, ethanol, 2-propanol, butanol and benzyl alcohol; hetero atom-containing organic solvents such as acetonitrile, DMF and DMSO. Preferred are alcohol solvents. The amount of the solvent may be determined depending on the solubility of the reaction substance and the economic potential thereof. For example, depending on the substance, the reaction may be carried out at a low solvent concentration of 1% or less, or nearly in the absence of a solvent. Preferably, the solvent is used in an amount of from 0.1 to 5.0 times by volume.

The reaction temperature may be from 0 to 150° C. but is more preferably within a range of from 10 to 70° C. The reaction time may depend on the reaction conditions such as concentration of reaction substances and temperature, the reaction may be finished in a few minutes to 30 hours. After the reaction, the system may be post-processed in an ordinary manner to isolate the intended optically active aldehyde (1).

After the reaction, the intended product may be isolated according to ordinary post-treatment and, if desired, according to a method of distillation, column chromatography, etc. The reaction mode in the present invention may be any of a batch system or a continuous system.

EXAMPLES

The present invention is described in detail below with reference to Examples, but the present invention is not limited by these Examples in any way.

Example 1

Asymmetric isomerization of (E)-3-phenyl-4-methyl-2-pentenol

[Chem. 7]

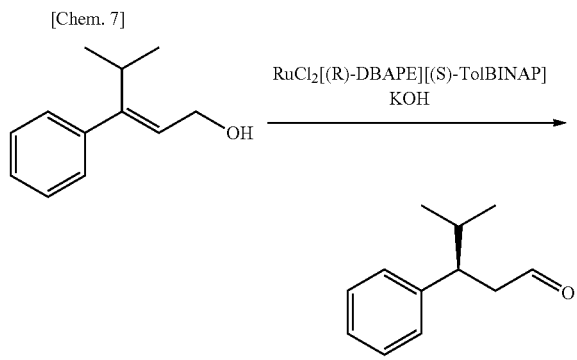

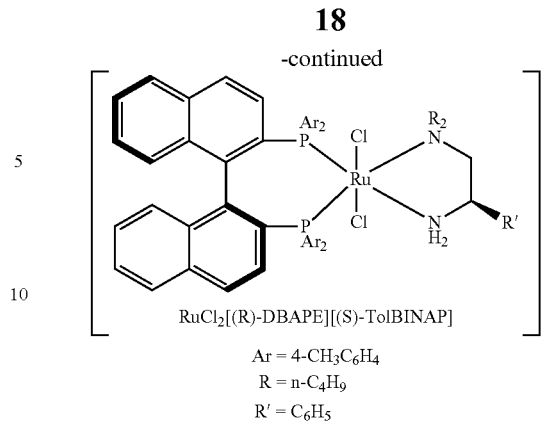

$Ar = 4\text{-}CH_3C_6H_4$
$R = n\text{-}C_4H_9$
$R' = C_6H_5$

RuCl$_2$[(S)-tolbinap][(R)-dbape](3.2 mg, 2.9 μmol, S/C=1000) and (E)-3-phenyl-4-methyl-2-pentenol (513.6 mg, 2.914 mmol) were added to a 50-mL Schlenk flask substituted with argon, and ethanol (13.6 mL) degassed by three freeze-pump-thaw cycles was transferred from a μ Schlenk flask using a Teflon (registered trade mark) cannula and added thereto. Further, an ethanol solution of potassium hydroxide (15 mM, 0.98 mL, 15 μmol) was added thereto, followed by stirring at 25° C. for 1 hour. After the catalyst and the base were removed by passing through a short column of silica gel, the solvent was removed by distillation under reduced pressure to obtain a mixture. The mixture was analyzed through gas chromatography (column: SPELCOSLB™-5 ms (0.25 mm×30 m, DF=0.25); carrier gas: helium (100 kPa); column temp.: 80° C. for 2 min, heating to 180° C. at a rate of 3° C. min$^{-1}$; injection temp.: 250° C.). As a result, (3R)-3-phenyl-4-methylpentanol was formed in a yield of 90%. (3R)-3-phenyl-4-methylpentanol was isolated by purification through silica gel column chromatography (411.4 mg, 80% in yield). The optical purity of this was measured through gas chromatography (GC analysis: column, Varian CHIRASIL-DEX CB (0.32 mm×25 m, DF=0.25); carrier gas: helium (60 kPa); column temp.: 50° C. for 12 min, heating to 145° C. at a rate of 1° C. min; injection temp.: 200° C.). As a result, it was >99% ee.

$^1$H NMR δ=0.77 (d, J=6.7 Hz, 3H), 0.95 (d, J=6.7 Hz, 3H), 1.26 (br s, 1H), 1.87 (m, 1H), 2.70-2.84 (m, 2H), 2.88-3.00 (m, 1H), 7.13-7.23 (m, 3H), 7.25-7.32 (m, 2H).

Examples 2 to 10

Reactions were carried out using (E)-3-phenyl-4-methyl-2-pentenol as a starting material in the same manner as in Example 1 except that the catalyst, the molar ratio of the substance to the catalyst and the reaction solvent which were used in Example 1 were changed as shown in Table 1. With regard to the yield of (3R)-3-phenyl-4-methylpentanol, after completion of the reactions, the solvents were concentrated under reduced pressure to obtain residues, and the yield was measured through gas chromatography (column: SPELCO SLB™-5 ms), in the same manner as in Example 1. The optical purity was also measured using gas chromatography (column: Varian CHIRASIL-DEX CB) in the same manner as in Example 1. The reaction results of Examples 1 to 10 are shown in Table 1.

[Chem. 8]

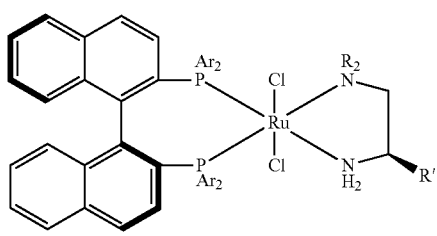

Catalyst [A]: Ar=4-CH₃C₆H₄, R=n-C₄H₉, R'=C₆H₅, RuCl₂[(R)-DBAPE][(S)-TolBINAP]

Catalyst [B]: Ar=4-CH₃C₆H₄, R=n-C₄H₉, R'=H, RuCl₂[DBAE][(S)-TolBINAP]

Catalyst [C]: [RuCl₂{(S)-TolBINAP}(dmf)ₙ]

Catalyst [D]: [RuCl{(S)-TolBINAP}(p-cymene)]Cl

Catalyst [E]: [(C₂H₅)₂NH₂][RuCl{(S)-TolBINAP}₂(μ-Cl)₃]

TABLE 1

| Example | Catalyst | Substance/Catalyst (molar ratio) | Solvent | Yield (%) | Optical Purity (% ee) |
|---|---|---|---|---|---|
| 1 | A | 1000 | EtOH | 90 | >99 |
| 2 | A | 2000 | EtOH | 78 | >99 |
| 3 | A | 1000 | i-PrOH | 55 | >99 |
| 4 | A | 1000 | MeOH | 45 | >99 |
| 5 | A | 900 | t-BuOH | 23 | >99 |
| 6 | A | 1000 | t-BuOH:MeOH = 3:1 | 79 | >99 |
| 7 | B | 1000 | EtOH | 84 | >99 |
| 8 | C | 1000 | EtOH | 82 | >99 |
| 9 | D | 1000 | EtOH | 48 | >99 |
| 10 | E | 1000 | EtOH | 77 | >99 |

As is apparent from Table 1, in all of Examples 1 to 10, an extremely high optical purity of 99% ee or more could be obtained.

Examples 11 to 22

Reactions were carried out in the same manner as in Example 1 except that the molar ratio of the substance to the catalyst and the reaction time in Example 1 were changed as shown in Table 2, and that starting materials shown in Table 2 were used. With regard to the reaction yield, after completion of the reactions, the solvents were concentrated under reduced pressure to obtain residues, and the yield was measured through gas chromatography (column: SPELCO SLB™-5 ms), in the same manner as in Example 1. The optical purity was also measured using gas chromatography (column: Varian CHIRASIL-DEX CB, SPELCO-DEX™ 225 only for compound (k) and compound (l)) in the same manner as in Example 1. Only for compound (c), an aldehyde as a product was reduced to an alcohol and acetylated by an ordinary method (NaBH₄, subsequently AcCl, pyridine), and thereafter, the optical purity was determined by the same method. The reaction results are shown in Table 2.

[Chem. 9]

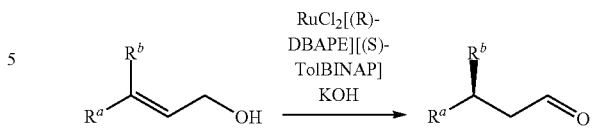

Compound (a): $R^a$=C₆H₅, $R^b$=i-C₃H₇
[(E)-3-phenyl-4-methyl-2-pentenol]
Compound (b): $R^a$=4-CH₃C₆H₄, $R^b$=i-C₃H₇
[(E)-3-(4-methylphenyl)-4-methyl-2-pentenol]
Compound (c): $R^a$=4-CH₃OC₆H₄, $R^b$=i-C₃H₇
[(E)-3-(4-methoxyphenyl)-4-methyl-2-pentenol]
Compound (d): $R^a$=4-ClC₆H₄, $R^b$=i-C₃H₇
[(E)-3-(4-chlorophenyl)-4-methyl-2-pentenol]
Compound (e): $R^a$=C₆H₅, $R^b$=cyclo-C₆H₁₁
[(E)-3-phenyl-3-cyclohexyl-2-propenol]
Compound (f): $R^a$=C₆H₅, $R^b$=C₂H₅
[(E)-3-phenyl-2-pentenol]
Compound (g): $R^a$=C₆H₅, $R^b$=CH₃
[(E)-3-phenyl-2-butenol]
Compound (h): $R^a$=i-C₃H₇, $R^b$=C₆H₅
[(Z)-3-phenyl-4-methyl-2-pentenol]
Compound (i): $R^a$=CF₃, $R^b$=C₆H₅
[(E)-3-trifluoromethyl-3-phenyl-2-propenol]
Compound (j): $R^a$=cyclo-C₆H₁₁, $R^b$=CH₃
[(E)-3-cyclohexyl-2-butenol]
Compound (k): $R^a$=(CH₃)₂C=CH(CH₂)₂, $R^b$=CH₃
[geraniol ((E)-3,7-dimethyl-2,6-octadien-1-ol)]
Compound (l): $R^a$=CH₃, $R^b$=(CH₃)₂C=CH(CH₂)₂
[nerol ((Z)-3,7-dimethyl-2,6-octadien-1-ol)]
Compound (m): $R^a$=n-C₄H₉, $R^b$=CH₃
[(E)-3-methyl-2-heptenol]

TABLE 2

| Example | Starting Material | Substance/Catalyst (molar ratio) | Reaction Time (hour) | Yield (%) | Optical Purity (% ee) |
|---|---|---|---|---|---|
| 1 | Compound (a) | 1000 | 1.0 | 90 | >99 |
| 11 | Compound (b) | 900 | 1.0 | 87 | >99 |
| 12 | Compound (c) | 1100 | 1.0 | 74 | 99 |
| 13 | Compound (d) | 900 | 1.0 | 92 | 99 |
| 14 | Compound (e) | 1000 | 0.5 | 92 | >99 |
| 15 | Compound (f) | 200 | 1.0 | 70 | >99 |
| 16 | Compound (g) | 100 | 1.0 | 50 | 99 |
| 17 | Compound (h) | 300 | 1.0 | 50 | >99 |
| 18 | Compound (i) | 400 | 1.0 | 53 | >99 |
| 19 | Compound (j) | 600 | 1.0 | 58 | >99 |
| 20 | Compound (k) | 200 | 1.0 | 58 | >99 |
| 21 | Compound (l) | 200 | 1.0 | 83 | >99 |
| 22 | Compound (m) | 100 | 1.0 | 75 | >99 |

As is apparent from Table 2, in all of Examples 1 and 11 to 22, an extremely high optical purity of 99% ee or more could be obtained.

While the invention has been described in detail and with reference to specific embodiments thereof, it will be apparent to one skilled in the art that various changes and modifications can be made therein without departing from the spirit and scope thereof. The present application is based on Japanese Patent Application No. 2013-044065 filed on Mar. 6, 2013, the contents of which are incorporated herein by reference.

The invention claimed is:

1. A method for producing an optically active aldehyde of the formula (1):

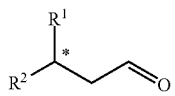 (1)

wherein $R^1$ and $R^2$ are each independently selected from the group consisting of an alkyl group having from 1 to 20 carbon atoms, which may have a substituent, an alkenyl group having from 2 to 20 carbon atoms, which may have a substituent, a 3- to 8-membered alicyclic group which may have a substituent, an aryl group having from 6 to 15 carbon atoms, which may have a substituent, and an aralkyl group having from 7 to 12 carbon atoms, which may have a substituent; $R^1$ and $R^2$ are groups different from each other; and * is an asymmetric carbon atom, the method comprising asymmetrically isomerizing an allyl alcohol of by the formula (2) in the presence of a ruthenium complex and a base in an ethanol solvent:

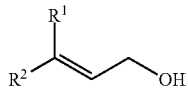 (2)

wherein $R^1$ and $R^2$ have the same meanings as described above, wherein the asymmetric isomerization is carried out using a ruthenium complex of the following general formula (3):

$$[Ru_m L_n W_p U_q]_r Z_s \quad (3)$$

wherein (a): L is an optically active bidentate phosphine ligand; W is a chlorine atom, a bromine atom or an iodine atom, Z is dimethylformamide or dimethylacetamide, m=n=r=1, p=2, q=0, and s is an integer of from 0 to 4;

(b): L is an optically active bidentate phosphine ligand; W is a chlorine atom, a bromine atom or an iodine atom, U is a chlorine atom, a bromine atom or an iodine atom, Z is a dialkylammonium ion, m=n=p=2, q=3, r=s=1; or (c): L is an optically active bidentate phosphine ligand: W and U may be the same or different, representing a hydrogen atom, a chlorine atom, a bromine atom, an iodine atom, a carboxyl group or any other anion group, Z is a diamine compound, m=n=p=q=r=s=1.

2. The method according to claim 1, wherein the reaction temperature is 0 to 70° C.

3. The method according to claim 1 wherein the reaction temperature is 0 to 25° C.

* * * * *